(12) United States Patent
Manassen et al.

(10) Patent No.: US 10,444,161 B2
(45) Date of Patent: Oct. 15, 2019

(54) SYSTEMS AND METHODS FOR METROLOGY WITH LAYER-SPECIFIC ILLUMINATION SPECTRA

(71) Applicant: KLA-Tencor Corporation, Milpitas, CA (US)

(72) Inventors: Amnon Manassen, Haifa (IL); Daria Negri, Nesher (IL); Andrew V. Hill, Berkley, CA (US); Ohad Bachar, Timrat (IL); Vladimir Levinski, Nazareth Ilit (IL); Yuri Paskover, Caesarea (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/608,766

(22) Filed: May 30, 2017

(65) Prior Publication Data

US 2018/0292326 A1   Oct. 11, 2018

Related U.S. Application Data

(60) Provisional application No. 62/481,685, filed on Apr. 5, 2017.

(51) Int. Cl.
*G01N 21/88* (2006.01)
*G01B 11/27* (2006.01)
(Continued)

(52) U.S. Cl.
CPC ..... *G01N 21/8806* (2013.01); *G01B 11/0633* (2013.01); *G01B 11/272* (2013.01);
(Continued)

(58) Field of Classification Search
CPC .............. G01B 11/0633; G01B 11/272; G01B 2210/56; G01N 2021/8438;
(Continued)

(56) References Cited

U.S. PATENT DOCUMENTS

| 15,339,312 | 10/2016 | Hill |
| 15,387,180 | 12/2016 | Hill |

(Continued)

OTHER PUBLICATIONS

International Search Report and Written Opinion dated Jul. 11, 2018 for PCT/US2018/024702.

*Primary Examiner* — Violeta A Prieto
(74) *Attorney, Agent, or Firm* — Suiter Swantz PC LLO

(57) ABSTRACT

A metrology system includes an image device and a controller. The image device includes a spectrally-tunable illumination device and a detector to generate images of a sample having metrology target elements on two or more sample layers based on radiation emanating from the sample in response to illumination from the spectrally-tunable illumination device. The controller determines layer-specific imaging configurations of the imaging device to image the metrology target elements on the two or more sample layers within a selected image quality tolerance in which each layer-specific imaging configuration includes an illumination spectrum from the spectrally-tunable illumination device. The controller further receives one or more images of the metrology target elements on the two or more sample layers generated using the layer-specific imaging configurations. The controller further provides a metrology measurement based on the one or more images of the metrology target elements on the two or more sample layers.

57 Claims, 6 Drawing Sheets

(51) Int. Cl.
*G01N 21/33* (2006.01)
*G01N 21/3563* (2014.01)
*G01N 21/95* (2006.01)
*G01N 21/84* (2006.01)
*G03F 7/20* (2006.01)
*G01B 11/06* (2006.01)

(52) U.S. Cl.
CPC ......... *G01N 21/33* (2013.01); *G01N 21/3563* (2013.01); *G01N 21/8422* (2013.01); *G01N 21/9505* (2013.01); *G03F 7/70633* (2013.01); *G01B 2210/56* (2013.01); *G01N 2021/8438* (2013.01); *G01N 2021/8845* (2013.01); *G01N 2201/06113* (2013.01)

(58) Field of Classification Search
CPC ........... G01N 2021/8845; G01N 21/33; G01N 21/3563; G01N 21/8422; G01N 21/8806; G01N 21/9505; G01N 2201/06113; G03F 7/70633
See application file for complete search history.

(56) References Cited

U.S. PATENT DOCUMENTS

| | | | |
|---|---|---|---|
| 9,958,784 B2* | 5/2018 | Luo | G03F 7/70325 |
| 2003/0043375 A1 | 3/2003 | Opsal | |
| 2006/0238754 A1* | 10/2006 | Fukazawa | G01N 21/956 356/237.2 |
| 2011/0085726 A1 | 4/2011 | Den Boer et al. | |
| 2013/0114085 A1 | 5/2013 | Wang et al. | |
| 2013/0169966 A1 | 7/2013 | Shchegrov et al. | |
| 2014/0136137 A1* | 5/2014 | Tarshish-Shapir | G06T 7/0004 702/108 |
| 2014/0168650 A1* | 6/2014 | Manassen | F21V 9/40 356/432 |
| 2014/0172394 A1 | 6/2014 | Kuznetsov et al. | |
| 2016/0290796 A1 | 10/2016 | Levy et al. | |
| 2017/0350575 A1* | 12/2017 | Hill | F21V 9/40 |
| 2018/0052099 A1* | 2/2018 | Hill | G03F 7/70633 |
| 2018/0087900 A1* | 3/2018 | Paskover | G01B 11/272 |

* cited by examiner

SYSTEMS AND METHODS FOR METROLOGY WITH LAYER-SPECIFIC ILLUMINATION SPECTRA

CROSS-REFERENCE TO RELATED APPLICATION

The present application claims the benefit under 35 U.S.C. § 119(e) of U.S. Provisional Application Ser. No. 62/481,685, filed Apr. 5, 2017, entitled OVERLAY METROLOGY WITH PROCESS LAYERS ILLUMINATED BY DIFFERENT SPECTRA, naming Amnon Manassen, Daria Negri, Andrew Hill, Ohad Bachar, Vladimir Levinski, and Yuri Paskover as inventors, which is incorporated herein by reference in the entirety.

TECHNICAL FIELD

The present disclosure relates generally to metrology systems, and more particularly, to multi-layer metrology with layer-specific configurations.

BACKGROUND

Metrology systems suitable for characterizing multi-layer samples such as semiconductor devices may analyze any number of layers on a sample. However, metrology measurements of any given layer may be influenced by surrounding material such that a given configuration of the metrology system may not provide the same degree of performance (e.g. precision, repeatability, or the like) for all sample layers. For example, metrology of a sub-surface layer may involve propagating an illumination beam through one or more transparent or semi-transparent layers near the surface and receiving radiation from the sub-surface layer through the transparent or semi-transparent layers. Accordingly, metrology performance may be highly layer-specific and may depend on particular aspects of the sample layout such as, but not limited to, the thickness of sample layers, optical properties of sample layers, or patterned features on sample layers. Therefore, it would be desirable to provide a system and method for curing defects such as those identified above.

SUMMARY

A metrology system is disclosed in accordance with one or more illustrative embodiments of the present disclosure. In one illustrative embodiment, the system includes an imaging device. In another illustrative embodiment, the image device includes a spectrally-tunable illumination device. In another illustrative embodiment, the image device includes a detector to generate images of a sample including metrology target elements on two or more sample layers based on radiation emanating from the sample in response to illumination from the spectrally-tunable illumination device. In another illustrative embodiment, the system includes a controller communicatively coupled to the imaging device. In another illustrative embodiment, the controller determines layer-specific imaging configurations of the imaging device to image the metrology target elements on the two or more sample layers within a selected image quality tolerance in which each layer-specific imaging configuration includes an illumination spectrum from the spectrally-tunable illumination device. In another illustrative embodiment, the controller receives, from the imaging device, the one or more images of the metrology target elements on the two or more sample layers generated using the layer-specific imaging configurations. In another illustrative embodiment, the controller provides a metrology measurement based on the one or more images of the metrology target elements on the two or more sample layers.

A metrology system is disclosed in accordance with one or more illustrative embodiments of the present disclosure. In one illustrative embodiment, the system includes an imaging device. In another illustrative embodiment, the imaging device includes a broadband illumination device. In another illustrative embodiment, the imaging device includes a spectrally-tunable filter to spectrally filter radiation emanating from the sample in response to illumination from the broadband illumination device. In another illustrative embodiment, the imaging device includes a detector to generate images of a sample including two or more sample layers based on the radiation emanating from the sample and filtered by the spectrally-tunable filter. In another illustrative embodiment, the system includes a controller communicatively coupled to the imaging device. In another illustrative embodiment, the controller determines layer-specific imaging configurations of the imaging device to image the metrology target elements on the two or more sample layers within a selected image quality tolerance in which each layer-specific imaging configuration includes a spectrum of radiation from the sample filtered by the spectrally-tunable filter. In another illustrative embodiment, the controller receives, from the detector, one or more images of the metrology target elements on the two or more sample layers generated using the layer-specific imaging configurations. In another illustrative embodiment, the controller provides a metrology measurement based on the one or more images of the metrology target elements on the two or more sample layers.

A method is disclosed in accordance with one or more illustrative embodiments of the present disclosure. In one illustrative embodiment, the method includes determining layer-specific imaging configurations of an imaging device to image metrology target elements on two or more sample layers of a sample within a selected image quality tolerance in which each layer-specific imaging configuration includes an imaging spectrum. In another illustrative embodiment, the method includes receiving, from the imaging device, one or more images of the metrology target elements on the two or more sample layers generated using the layer-specific imaging configurations. In another illustrative embodiment, the method includes providing a metrology measurement based on the one or more images of the metrology target elements on the two or more sample layers.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1:
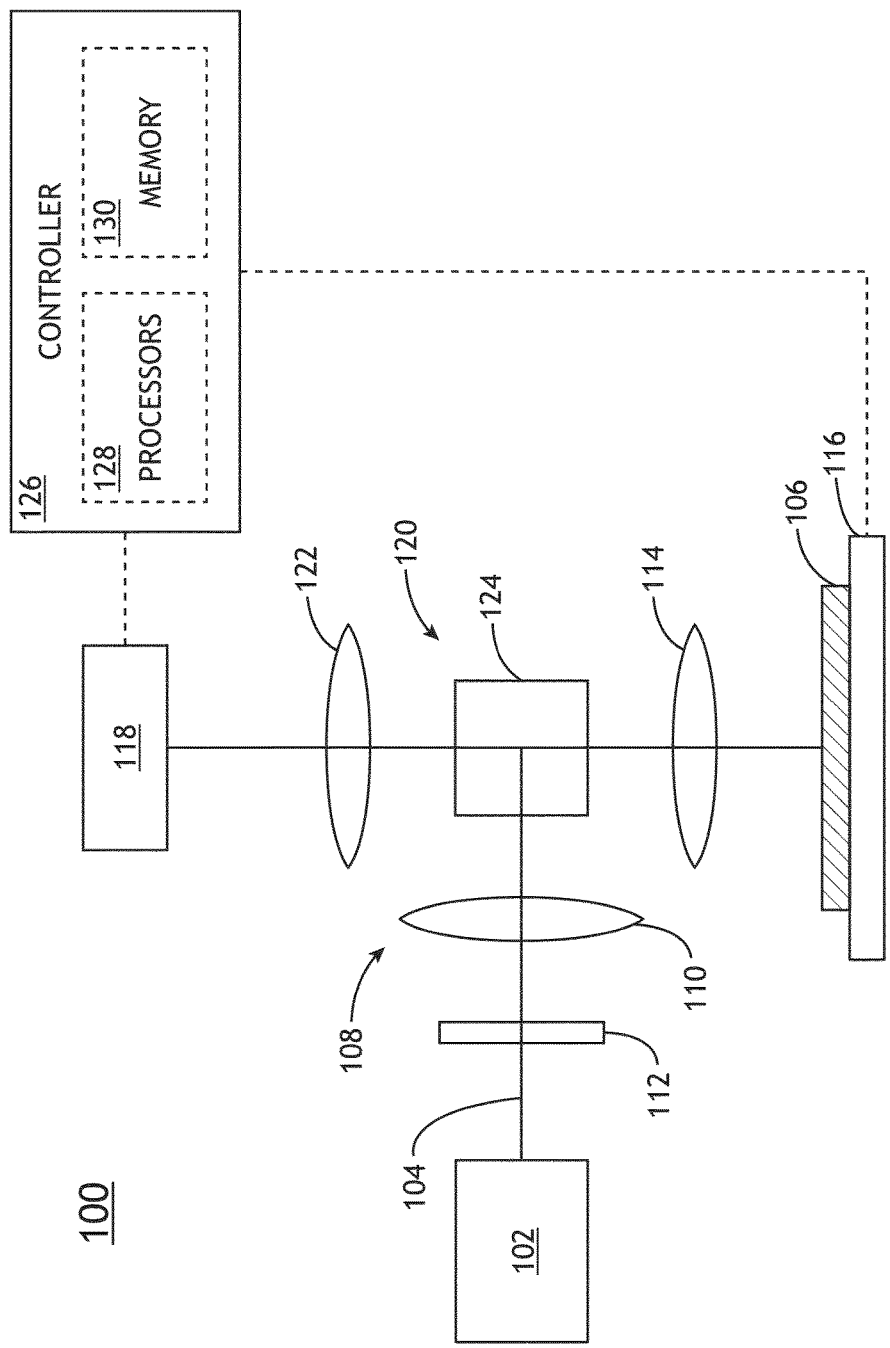
FIG. 1 is a conceptual view illustrating an imaging device, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to systems and methods for imaging multiple layers of a sample using layer-specific imaging configurations. For example, an imaging configuration may include, but is not limited to, a spectrum of illumination incident on a sample to be imaged, an illumination profile, a spectrum of radiation incident on a detector, a position of the sample within a focal volume (e.g. focal position), configurations of field stops, configurations of aperture stops (e.g. to modify image and/or object-space telecentricity, or the like), or detector parameters (e.g. gain, integration time, or the like). Accordingly, embodiments of the present disclosure are directed to generating a tailored imaging configuration for accurate imaging of features located on different layers of interest on a sample.

It is recognized herein that imaging systems may generate an image of a sample layer by illuminating the sample and detecting radiation emanating from the sample in response to the illumination. In a general sense, radiation may emanate from any layer of a sample in response to incident illumination through a wide range of interaction mechanisms including, but not limited to, reflection, scattering, diffraction, or luminescence. Further, an imaging system may generate a focused image of features within a depth of field defined at least in part by the spectrum of illumination and the numerical aperture (NA) of the system. An imaging system may thus be configured to image features on the surface of a sample as well as sub-surface features of a semi-transparent sample within the depth of field.

Sub-surface layers may be imaged by propagating illumination through any near-surface layers and detecting radiation based on interaction with a sub-surface layer of interest. Radiation emanating from a sub-surface layer of interest may further propagate through the near-surface layers to reach a detector. The resulting imaging signal associated with a sub-surface layer may thus be influenced by the near-surface layers. For example, near-surface layers may absorb certain wavelengths of illumination. Additionally, near-surface layers may refract illumination at any interfaces between different materials on a single layer or between layers, which may modify the focusing of illumination and/or introduce dispersion to generate wavelength-dependent optical paths through the sample (e.g. chromatic aberration). Patterned features on any sample layer may further impact the resulting imaging signal through scattering and/or diffraction.

Accordingly, it may be the case that image quality may vary for features on different sample layers when imaged using a single imaging configuration due to differences in optical paths between the sample layers. Image quality may be measured according to any metric such as, but not limited to image contrast, image brightness, or image noise. Further, even if an imaging configuration is tailored to provide an image of two or more sample layers (e.g. by generating a tailored illumination spectrum, or the like), it may be the case that the tailored imaging configuration may not provide images of each layer of interest within desired tolerances based on one or more image quality metrics. Additional embodiments of the present disclosure are directed to generating tailored layer-specific imaging configurations for multiple sample layers of interest to provide images of features on each sample layer of interest within selected image quality tolerances.

It is further recognized herein that the precision and/or the repeatability of metrology measurements based on images of different layers of a sample may vary based on the image quality. For example, the spectral content of illumination may impact the perceived positions of features differently for different sample layers. Such variations in the perceived positions of features in an image of a sample layer may be particularly problematic in overlay metrology in which the relative positions of features on multiple layers are utilized to determine overlay errors.

Additional embodiments are directed to performing metrology measurements on two or more layers of a sample using layer-specific imaging configurations. Further, layer-specific imaging configurations may be used with any metrology system known in the art to provide metrology performance within selected tolerances. For example, image-based overlay metrology may be performed by imaging overlay target features on two or more layers of interest with tailored layer-specific metrology conditions and determining overlay error of the layers based on the layer-specific images. In this regard, overlay target features on each layer may be imaged with layer-specific imaging configurations tailored based on the particular sample to provide images having an image quality metric within a selected tolerance. By way of another example, a metrology system may measure one or more aspects of patterned features on sample layers (e.g. critical dimensions, sidewall angles, or the like) using layer-specific imaging configurations.

The metrology measurements on the two or more layers generated using layer-specific imaging configurations may be performed sequentially or simultaneously. For example, a metrology measurement may be performed for a first layer of interest using a first set of metrology conditions followed by a metrology measurement for a second layer of interest using a second set of metrology conditions, and so on. By way of another example, metrology measurements of spatially-separated features on different sample layers may be simultaneously performed using layer-specific metrology configurations. For instance, spatially-separated features on different sample layers (e.g. features of an overlay metrology target located on multiple sample layers) may be simultaneously illuminated with different layer-specific illumination spectra to provide a single image on a detector having a selected image quality tolerance for features in all layers of interest.

Additional embodiments are directed to determining layer-specific metrology configurations for two or more layers of a sample. For example, layer-specific metrology configurations may be determined by simulating metrology of each sample layer of interest based on a three-dimensional representation of a multi-layer sample. By way of another example, layer-specific metrology configurations may be determined experimentally based on a series of metrology measurements for each sample layer of interest with varying metrology conditions. Additional embodiments are directed to providing metrology measurements with layer-specific metrology configurations for two or more layers of a sample.

Additional embodiments are directed to metrology systems suitable for providing layer-specific metrology on multi-layer samples. For example, a metrology system suitable for providing layer-specific metrology measurements may include, but is not required to include, a spectrally-tunable illumination device for generating layer-specific illumination spectra, spectrally-tunable filters, a translatable sample stage for providing a layer-specific sample position, configurable field stops, configurable aperture stops (e.g. for adjusting image and/or object-space telecentricity), or a detector with configurable parameters (e.g. gain, integration time, or the like).

FIG. 1 is a conceptual view illustrating an imaging device 100, in accordance with one or more embodiments of the present disclosure. Further, the imaging device 100 may include a metrology device for determining one or more metrology measurements based on images generated by the imaging device 100. In this regard, the imaging device 100 may measure alignment using any method known in the art. In one embodiment, the imaging device 100 includes an image-based metrology tool to perform metrology measurements (e.g. overlay measurements, feature size measurements, or the like) based on one or more images of sample layers. In another embodiment, the imaging device 100 includes a scatterometry-based metrology tool to perform metrology measurements based on the scattering (reflection, diffraction, diffuse scattering, or the like) of light from the sample.

In one embodiment, the imaging device 100 includes an illumination source 102 to generate an illumination beam 104. The illumination beam 104 may include one or more selected wavelengths of light including, but not limited to, vacuum ultraviolet radiation (VUV), deep ultraviolet radiation (DUV), ultraviolet (UV) radiation, visible radiation, or infrared (IR) radiation. The illumination source 102 may further generate an illumination beam 104 including any range of selected wavelengths. In another embodiment, the illumination source 102 may include a spectrally-tunable illumination source to generate an illumination beam 104 having a tunable spectrum.

The illumination source 102 may further produce an illumination beam 104 having any temporal profile. For example, the illumination beam 104 generated by the illumination source 102 may include a continuous profile, a pulsed profile, or a modulated profile. Additionally, the illumination beam 104 may be delivered from the illumination source 102 via free-space propagation or guided light (e.g. an optical fiber, a light pipe, or the like).

In another embodiment, the illumination source 102 directs the illumination beam 104 to a sample 106 via an illumination pathway 108. In another embodiment, the imaging device 100 includes an objective lens 114 to focus the illumination beam 104 onto the sample 106.

The illumination pathway 108 may include one or more lenses 110 or additional optical components 112 suitable for modifying and/or conditioning the illumination beam 104. For example, the one or more optical components 112 may include, but are not limited to, one or more polarizers, one or more filters, one or more beam splitters, one or more diffusers, one or more homogenizers, one or more apodizers, or one or more beam shapers. By way of another example, the one or more optical components 112 may include aperture stops to control the angle of illumination on the sample 106 and/or field stops to control the spatial extent of illumination on the sample 106. In one instance, the illumination pathway 108 includes an aperture stop located at a plane conjugate to the back focal plane of the objective lens 114 to provide telecentric illumination of the sample. In another embodiment, the sample 106 is disposed on a sample stage 116. The sample stage 116 may include any device suitable for positioning the sample 106 within the imaging device 100. For example, the sample stage 116 may include any combination of linear translation stages, rotational stages, tip/tilt stages or the like.

In another embodiment, the imaging device 100 includes a detector 118 configured to capture radiation emanating from the sample 106 through a collection pathway 120. For example, the collection pathway 120 may include, but is not required to include, a collection lens (e.g. the objective lens 114 as illustrated in FIG. 1) or one or more additional collection pathway lenses 122. By way of another example, a detector 118 may receive radiation reflected or scattered (e.g. via specular reflection, diffuse reflection, and the like) from the sample 106. By way of another example, a detector 118 may receive radiation generated by the sample 106 (e.g. luminescence associated with absorption of the illumination beam 104, or the like).

The detector 118 may include any type of optical detector known in the art suitable for measuring illumination received from the sample 106. For example, a detector 118 may include, but is not limited to, a CCD detector, a TDI detector, a photomultiplier tube (PMT), an avalanche photodiode (APD), or the like. In another embodiment, a detector 118 may include a spectroscopic detector suitable for identifying wavelengths of radiation emanating from the sample 106. In another embodiment, the imaging device 100 may include multiple detectors 118 (e.g. associated with multiple beam paths generated by one or more beamsplitters to facilitate multiple metrology measurements by the imaging device 100.

The collection pathway 120 may further include any number of optical elements to direct and/or modify illumination collected by the objective lens 114 including, but not limited to one or more collection pathway lenses 122, one or more filters, one or more polarizers, or one or more beam blocks. Additionally, the collection pathway 120 may include field stops to control the spatial extent of the sample imaged onto the detector 118 or aperture stops to control the angular extent of illumination from the sample used to generate an image on the detector 118. In another embodiment, the collection pathway 120 includes an aperture stop located in a plane conjugate to the back focal plane of an optical element the objective lens 114 to provide telecentric imaging of the sample.

In one embodiment, as illustrated in FIG. 1A, the imaging device 100 includes a beamsplitter 124 oriented such that the objective lens 114 may simultaneously direct the illumination beam 104 to the sample 106 and collect radiation emanating from the sample 106. In this regard, the imaging device 100 may be configured in an epi-illumination mode.

In another embodiment, the angle of incidence of the illumination beam 104 on the sample 106 is adjustable. For example, the path of the illumination beam 104 through the beamsplitter 124 and the objective lens 114 may be adjusted to control the angle of incidence of the illumination beam 104 on the sample 106. In this regard, the illumination beam 104 may have a nominal path through the beamsplitter 124 and the objective lens 114 such that the illumination beam 104 has a normal incidence angle on the sample 106. By way of another example, the angle of incidence of the illumination beam 104 on the sample 106 may be controlled by modifying the position and/or angle of the illumination beam 104 on the beamsplitter 124 (e.g. by rotatable mirrors, a spatial light modulator, a free-form illumination source, or the like). In another embodiment, the illumination source 102 directs the one or more illumination beam 104 to the sample 106 at an angle (e.g. a glancing angle, a 45-degree angle, or the like).

In another embodiment, the imaging device 100 includes a controller 126. In another embodiment, the controller 126 includes one or more processors 128 configured to execute program instructions maintained on a memory medium 130. In this regard, the one or more processors 128 of controller 126 may execute any of the various process steps described throughout the present disclosure. Further, the controller 126 may be configured to receive data including, but not limited to, metrology data (e.g. alignment measurement results, images of the target, pupil images, and the like) or metrology metrics (e.g. precision, tool-induced shift, sensitivity, diffraction efficiency, and the like).

The one or more processors 128 of a controller 126 may include any processing element known in the art. In this sense, the one or more processors 128 may include any microprocessor-type device configured to execute algorithms and/or instructions. In one embodiment, the one or more processors 128 may consist of a desktop computer, mainframe computer system, workstation, image computer, parallel processor, or any other computer system (e.g., networked computer) configured to execute a program configured to operate the imaging device 100, as described throughout the present disclosure. It is further recognized that the term "processor" may be broadly defined to encompass any device having one or more processing elements, which execute program instructions from a non-transitory memory medium 130. Further, the steps described throughout the present disclosure may be carried out by a single controller 126 or, alternatively, multiple controllers. Additionally, the controller 126 may include one or more controllers housed in a common housing or within multiple housings. In this way, any controller or combination of controllers may be separately packaged as a module suitable for integration into imaging device 100. Further, the controller 126 may analyze data received from the detector 118 and feed the data to additional components within the imaging device 100 or external to the imaging device 100.

The memory medium 130 may include any storage medium known in the art suitable for storing program instructions executable by the associated one or more processors 128. For example, the memory medium 130 may include a non-transitory memory medium. By way of another example, the memory medium 130 may include, but is not limited to, a read-only memory, a random access memory, a magnetic or optical memory device (e.g., disk), a magnetic tape, a solid state drive and the like. It is further noted that memory medium 130 may be housed in a common controller housing with the one or more processors 128. In one embodiment, the memory medium 130 may be located remotely with respect to the physical location of the one or more processors 128 and controller 126. For instance, the one or more processors 128 of controller 126 may access a remote memory (e.g., server), accessible through a network (e.g., internet, intranet and the like). Therefore, the above description should not be interpreted as a limitation on the present invention but merely an illustration.

In another embodiment, the controller 126 is communicatively coupled to one or more elements of the imaging device 100 to provide layer-specific metrology configuration information. For example, the controller 126 may be, but is not required to be, communicatively coupled to the illumination source 102 to control the spectrum of illumination incident on the sample, to one or more stops to manipulate the illumination beam 104 and/or radiation from the sample captured by the detector 118, to the detector 118 to modify detection parameters, or to the sample stage 116 to adjust the position of the sample 106 within the imaging device 100.

In one embodiment, a layer-specific imaging configuration includes a layer-specific spectrum of illumination incident on the sample 106. Accordingly, the illumination source 102 may be configured as a spectrally-tunable illumination source to provide layer-specific illumination spectra for metrology. It is recognized herein that the illumination source 102 may include a source of illumination and any number of additional components to condition illumination from the illumination source. Further, the additional components may share a common container with the illumination source 102 or may be integrated into the imaging device 100.

Figure 2A:
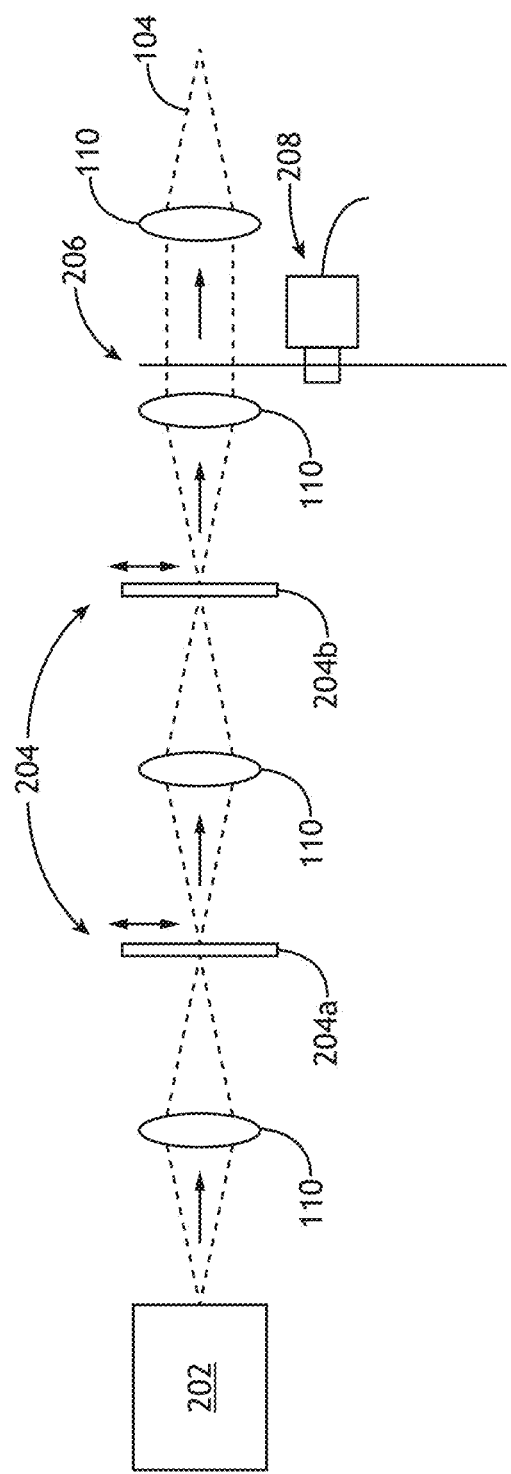
FIG. 2A is a conceptual view of a spectrally-tunable illumination source, in accordance with one or more embodiments of the present disclosure.
Figure 2B:
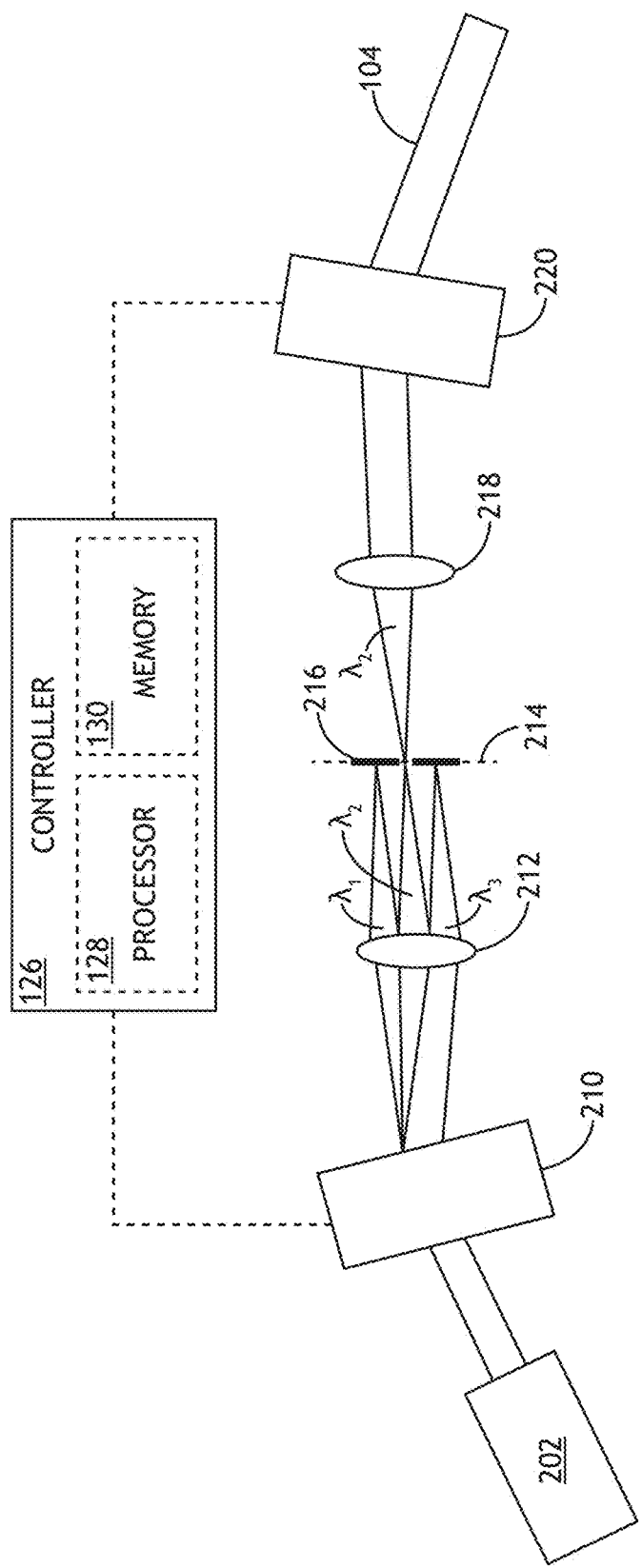
FIG. 2B is a conceptual view of an illumination source including a broadband source and a double monochromator to selectively filter the spectrum of the broadband source, in accordance with one or more embodiments of the present disclosure.
Figure 2C:
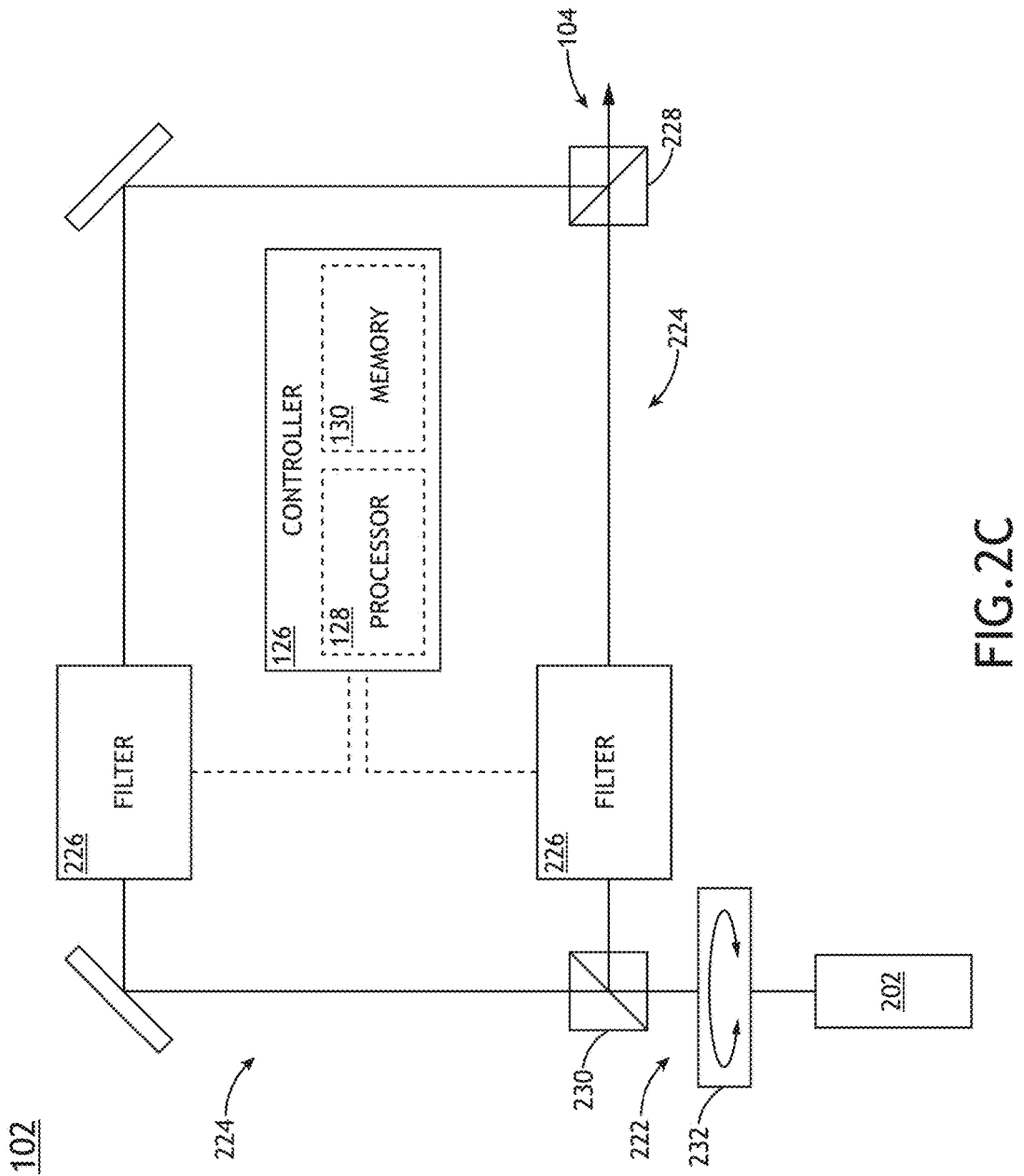
FIG. 2C is a conceptual view of a multi-channel illumination source including a broadband source and multiple filtering channels having fixed spectral transmittance, in accordance with one or more embodiments of the present disclosure.

FIGS. 2A through 2C illustrate spectrally-tunable illumination sources, in accordance with embodiments of the present disclosure.

FIG. 2A is a conceptual view of a spectrally-tunable illumination source 102, in accordance with one or more embodiments of the present disclosure. In one embodiment, the illumination source 102 includes a broadband source 202 having a broad spectrum (e.g. a range of wavelengths of illumination) and a tunable spectral filter 204 to filter the spectrum of the broadband source 202 to generate a layer-specific illumination spectrum. In another embodiment, the illumination source 102 includes a neutral density filter 206 (e.g. a wavelength-independent filter) to adjust the power of the illumination beam 104. The neutral density filter 206 may include any type of wavelength-independent filter known in the art such as, but not limited to, a polarization rotator coupled with a polarizer, one or more filters with a fixed optical density, or a gradient filter having an optical density that varies as a function of position across the filter. Further, the neutral density filter 206 may include a filter control device 208 to selectively modify the transmittance of the neutral density filter 206. For example, the filter control device 208 may include, but is not limited to, an adjustable polarization rotator to selectively adjust the polarization of the illumination beam 104 prior to a polarizer, a filter wheel to selectively place one of several filters in the path of the illumination beam 104 (e.g. as illustrated in FIG. 2A), or a translation device to selectively position a gradient filter (e.g. a rotation device, a linear translation device, or the like).

The broadband source 202 may include any source of illumination suitable for providing an illumination beam 104 having a range of wavelengths for metrology. In one embodiment, the broadband source 202 is a laser source. For example, the broadband source 202 may include, but is not limited to, a broadband laser source, a supercontinuum laser source, a white light laser source, or the like. In this regard, the broadband source 202 may provide an illumination beam 104 having high coherence (e.g. high spatial coherence and/or temporal coherence). In another embodiment, the broadband source 202 includes a laser-sustained plasma (LSP) source. For example, the broadband source 202 may include, but is not limited to, a LSP lamp, a LSP bulb, or a LSP chamber suitable for containing one or more elements that, when excited by a laser source into a plasma state, may emit broadband illumination. In another embodiment, the broadband source 202 includes a lamp source. For example, the broadband source 202 may include, but is not limited to, an arc lamp, a discharge lamp, an electrode-less lamp, or the like. In this regard, the broadband source 202 may provide an illumination beam 104 having low coherence (e.g. low spatial coherence and/or temporal coherence).

A tunable spectral filter 204 may modify the spectrum of incident illumination (e.g. the illumination beam 104 generated by the broadband source 202) by reducing the spectral power of select wavelengths relative to others. Accordingly, a spectral transmittance of a spectral filter may describe the transmittance of illumination as a function of wavelength (e.g. from 0% to 100%, 0 to 1, or the like). It is noted that transmittance may refer to illumination passed by the filter through transmission and/or reflection. A typical spectral filter may include, but is not required to include, one or more wavelength-dependent filters or one or more spatial filters located in a lens Fourier plane in which the spectral content is spatially distributed. Further, the tunable spectral filter 204 may modify the spectral transmittance according to any distribution. For example, the tunable spectral filter 204 may include a low-pass filter to attenuate wavelengths above a cutoff wavelength, a high-pass filter to attenuate wavelengths below a cutoff wavelength, a band-pass filter to pass a defined spectral bandwidth of illumination and attenuate wavelengths outside of a select band of wavelengths, a band-reject filter to attenuate wavelengths within a select band of wavelengths, a filter having a tailored spectral transmittance distribution, or the like.

The tunable spectral filter 204 may include any type of device suitable for filtering the spectrum of the broadband source 202. In one embodiment, the tunable spectral filter 204 includes one or more filters having tunable spectral transmittance. In this regard, the spectral transmittance of a tunable filter in the path of the illumination beam 104 may be selectively modified to provide layer-specific illumination spectra. For example, the tunable spectral filter 204 may include, but is not required to include, a thin film tunable filter formed from one or more stacked layers of dielectric material. Further, the tunable spectral filter 204 may include reflective spectral filters or transmissive spectral filters. In addition, a spectral filter may be formed from a single optical element or a combination of optical elements.

In another embodiment, the tunable spectral filter 204 includes one or more components having an orientation-dependent spectral transmittance. For example, as illustrated in FIG. 2A, the tunable spectral filter 204 may include one or more edge filters (e.g. edge filter 204a, edge filter 204b) having a position-sensitive cutoff wavelength that varies (e.g. linearly) across the filter. Accordingly, layer-specific illumination spectra may be obtained by adjusting the positions of the edge filters 204a,204b with respect to the path of the illumination beam 104 (e.g. via the controller 126). By way of another example, the tunable spectral filter 204 may include an angularly-tunable filter coupled to a rotation device to selectively modify the angle of incidence of the illumination beam 104 on the angularly-tunable filter.

In another embodiment, the tunable spectral filter 204 includes one or more filters having a fixed spectral transmittance and a filter insertion device to selectively insert the filters into a path of the illumination beam 104 to provide layer-specific illumination spectra. The filter insertion device may include any combination of elements suitable for selectively inserting filters into the path of the illumination beam 104. For example, the filter insertion device may include components for selectively rotating one or more filters into the path of the illumination beam 104 such as, but not limited to, a filter wheel or a flipper device. By way of another example, the filter insertion device may include components for linearly translating one or more filters into the path of the illumination beam 104 such as, but not limited to a mount for securing one or more filters attached to a linearly translatable stage.

In another embodiment, the tunable spectral filter 204 includes at least one dispersive element coupled with a spatial filter to modify the spectrum of the broadband source 202. FIG. 2B is a conceptual view of an illumination source 102 including a broadband source 202 and a double monochromator to selectively filter the spectrum of the broadband source 202, in accordance with one or more embodiments of the present disclosure. Systems and methods for spectral tuning of broadband light sources using double monochromators are described generally in U.S. patent application Ser. No. 15/339,312, filed on Oct. 31, 2016, which is incorporated herein by reference in its entirety. In one embodiment, the tunable spectral filter 204 includes a first tunable dispersive element 210 to introduce spectral dispersion to illumination from the broadband source 202, a first optical element 212 (e.g. one or more lenses, or the like) to focus the spectrally-dispersed illumination from the broadband source 202 to a focal plane 214 such that the spectrum of the illumination from the broadband source 202 may be spatially distributed across the focal plane 214, a spatial filtering element 216 to filter the illumination from the broadband source 202 based on the distribution of the spectrum at the focal plane, a second optical element 218 (e.g. one or more lenses, or the like) to collect the spectrally-dispersed illumination passed by the spatial filtering element 216, and a second tunable dispersive element 220 to remove the dispersion introduced by the first tunable dispersive element 210 to form the illumination beam 104.

For example, the first tunable dispersive element 210 may spectrally disperse the illumination from the broadband source 202 such that the spectrum of illumination from the broadband source 202 may be spatially distributed across the beam profile at the focal point of the first tunable dispersive element 210. The spatial filtering element 216 may selectively pass or block portions of the illumination from the broadband source 202. In this regard, a spectral transmittance of the tunable spectral filter 204 may be related to a spatial transmittance of the spatial filtering element 216. For instance, as illustrated in FIG. 2B, the illumination from the broadband source 202 may include three wavelength components $\lambda_1$, $\lambda_2$, and $\lambda_3$ and the spatial filtering element 216 may selectively pass $\lambda_2$ to form a layer-specific illumination spectrum. Further, the second tunable dispersive element 220 may remove the spectral dispersion introduced by the first tunable dispersive element 210 and collected by the second optical element 218 such that the spectrum of illumination from the broadband source 202 is no longer spatially distributed across the beam profile. For example, the dispersion of the second tunable dispersive element 220 may be dynamically adjusted to correspond to the dispersion of the first tunable dispersive element 210 to remove the dispersion introduced by the first tunable dispersive element 210. Accordingly, the tunable spectral filter 204 may filter the spectral content of the illumination from the broadband source 202 without modifying additional beam characteristics (e.g. divergence angle, or the like).

The dispersive elements (e.g. the first tunable dispersive element 210 or the second tunable dispersive element 220) may be any type of dispersive element known in the art suitable for introducing spectral dispersion into the illumination from the broadband source 202. For example, the dispersive elements may modify the dispersion into the illumination from the broadband source 202 through any mechanism such as, but not limited to, diffraction or refraction. Further, the first tunable dispersive element 210 may be formed from transmissive and/or reflective optical elements. In one instance, the first tunable dispersive element 210 includes a dynamically-generated diffraction grating (e.g. an acousto-optic modulator, or the like). In this regard, a diffraction grating may be dynamically generated in a substrate material (e.g. a transparent optical material). Further, the dispersion may be dynamically modified in order to tune the tunable spectral filter 204 by adjusting the physical characteristics of the dynamically-generated diffraction grating. For example, the period or the modulation depth of a dynamically-generated diffraction grating may be adjusted (e.g. via the controller 126) to control the value of dispersion (e.g. the angles at which particular wavelengths of illumination are diffracted). By way of another example, the modulation depth of the dynamically-generated diffraction grating may be adjusted (e.g. via the controller 126) to control the efficiency of dispersion (e.g. an efficiency value at which a particular wavelength of illumination is diffracted).

In another embodiment, the illumination source 102 includes a multi-channel illumination source. Multi-channel illumination sources for high-speed spectral selection are described generally in U.S. patent application Ser. No. 15/387,180, filed on Dec. 21, 2016, which is incorporated herein by reference in its entirety. FIG. 2C is a conceptual view of a multi-channel illumination source including a broadband source 202 and multiple filtering channels having fixed spectral transmittance, in accordance with one or more embodiments of the present disclosure. In one embodiment, a multi-channel illumination source includes a channel selector 222 to direct illumination from the broadband source 202 into two or more filtering channels 224 in which each of the filtering channels 224 includes a filter 226 with a different spectral transmissivity. Further, the multi-channel illumination source may include a beam combiner 228 to combine illumination from any of the filtering channels 224 as the illumination beam 104. Accordingly, a multi-channel illumination source may provide layer-specific illumination spectra by adjusting the channel selector 222 (e.g. via the controller 126) to direct illumination from the broadband source 202 through a selected one or more filtering channels 224.

The channel selector 222 may include any optical element or set of optical elements suitable for directing illumination from the broadband source 202 into any combination of filtering channels 224. For example, the channel selector 222 may include one or more beamsplitters 230. By way of another example, the channel selector 222 may include one or more dichroic mirrors. By way of a further example, as illustrated in FIG. 2C, the channel selector 222 may include a polarization rotator 232 (e.g. a waveplate, an electro-optical cell, or the like). Further, the channel selector 222 may include one or more polarized beamsplitters (e.g. beamsplitters 230, or the like). In this regard, the relative intensity of the illumination in the filtering channels 224 may be controllable by adjusting the polarization rotator 232 with respect to the orientation of a polarized beam splitter. Additionally, the channel selector 222 may include one or more shutters to control the distribution of illumination into the filtering channels 224.

A multi-channel illumination source may provide one or more beams associated with layer-specific illumination spectra to be directed to a sample. In this regard, an imaging device 100 including a multi-channel illumination source with independent spectral control for each of the filtering channels 224 may illuminate a sample with selectively controlled spectra over a broad continuous range of wavelengths. Additionally, the multi-channel illumination source may illuminate the sample with illumination from each channel simultaneously or sequentially. Further, the multi-channel illumination source may illuminate different portions of a sample (e.g. different cells of a metrology target, or the like) with different channels of illumination. In this regard, a multi-channel illumination source may provide different layer-specific illumination spectra to different regions of the sample (e.g. features of a metrology target located on different layers, or the like).

In another embodiment (not shown), the illumination source 102 includes multiple narrow-band illumination sources and a source selector to provide a layer-specific illumination spectrum including any combination of illumination from the narrow-band illumination sources. For example, the narrow-band illumination sources may include, but are not required to include, laser sources having different spectral characteristics. Further, the source selector may include any combination of elements suitable for selecting illumination from one or more narrow-band illumination sources. For example, the source selector may include, but is not limited to, one or more beamsplitters, one or more shutters, one or more waveplates, one or more polarizers, one or more beam combiners, or one or more shutters.

In another embodiment, a layer-specific imaging configuration includes a layer-specific detection spectrum. For example, the illumination source 102 may be configured with a fixed spectrum (e.g. a broadband spectrum) and the imaging device 100 may further include a tunable spectral filter to tailor the spectrum of radiation emanating from the sample 106 used to generate an image on the detector 118. In one instance, the imaging device 100 may include a tunable spectral filter in the collection pathway 120 prior to the detector for providing layer-specific detection spectra. The tunable spectral filter may include any type of tunable filter such as, but not limited to, a selectable set of filters with fixed spectral transmittances, one or more filters having orientation-dependent spectral transmittances, or the like.

In another embodiment, though not shown, the collection pathway 120 of imaging device 100 includes two or more detectors 118 for simultaneous generation of images of the sample filtered according to two or more layer-specific detection spectra. For example, the collection pathway 120 may include one or more beamsplitters to split radiation emanating from the sample into two or more detection channels. Each detection channel may further include a filter to provide a layer-specific detection spectrum and a detector 118 to generate an image of the sample with the layer-specific detection spectrum.

Figure 3:
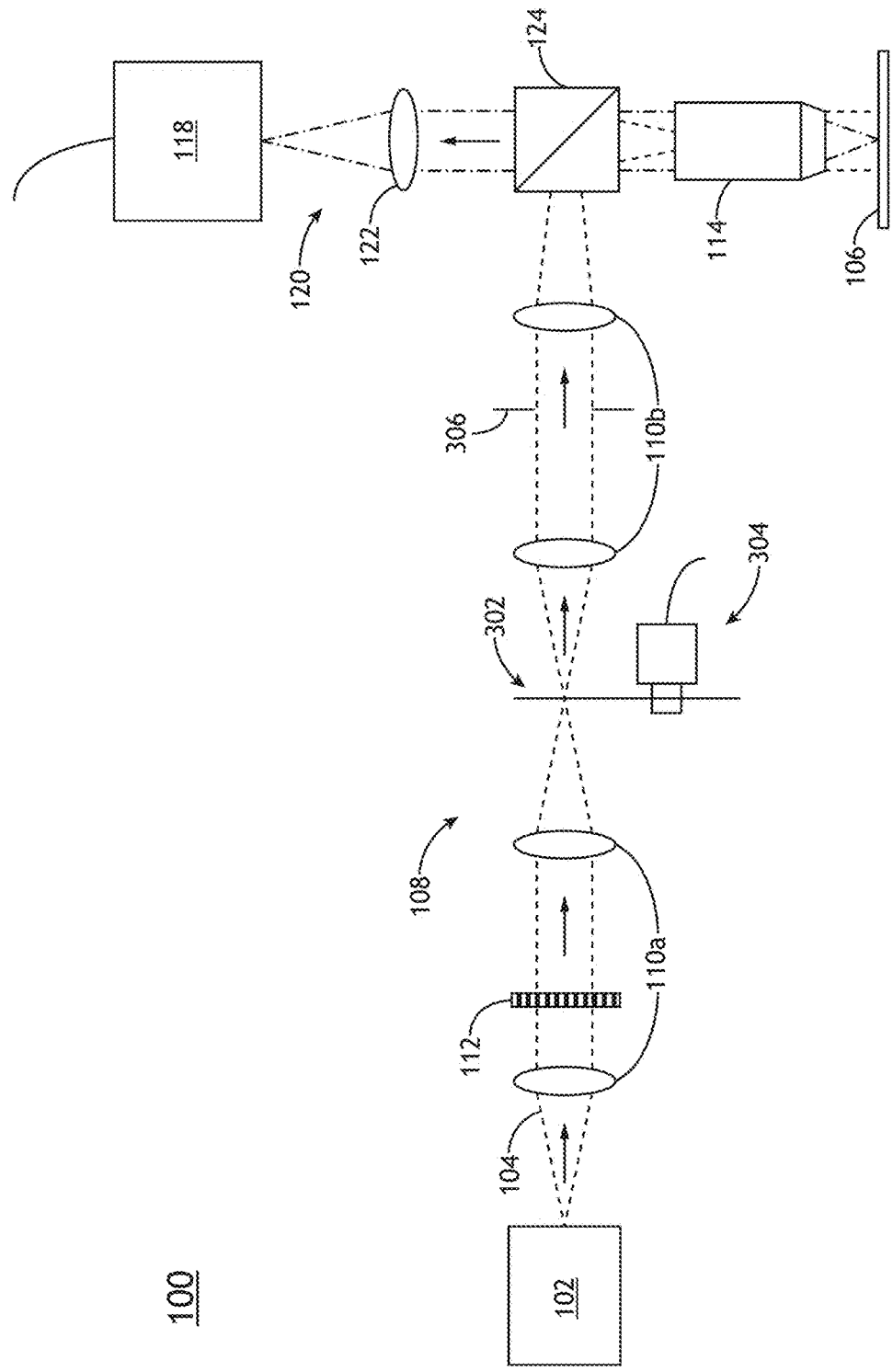
FIG. 3 is a conceptual view of an imaging device, in accordance with one or more embodiments of the present disclosure.

A layer-specific imaging configuration may include positions and/or open diameters of one or more stops within the system to tailor the paths of light within the imaging device 100. FIG. 3 is a conceptual view of a imaging device 100, in accordance with one or more embodiments of the present disclosure. In one embodiment, the imaging device 100 includes one or more aperture stops. In a general sense, an aperture stop may limit the angular extent of illumination propagating through the system. For example, as illustrated in FIG. 3, an aperture stop 302 in the illumination pathway 108 may provide a layer-specific angular extent of illumination on the sample. By way of another example (not shown), an aperture stop in the collection pathway 120 may provide a layer-specific limit of the angular extent of radiation emanating from the sample used to generate an image.

In another embodiment, a layer-specific imaging configuration includes an open diameter of an aperture stop in the illumination pathway 108 and/or the collection pathway 120. Accordingly, the imaging device 100 may include an aperture stop having an adjustable open diameter (e.g. coupled to the controller 126) for the generation of a layer-specific imaging configuration.

In another embodiment, a layer-specific imaging configuration includes a position of an aperture stop in the illumination pathway 108 and/or the collection pathway 120. For example, an aperture stop located at a plane conjugate to a focal point of the objective lens 114 in the illumination pathway 108 (e.g. aperture stop 302) may provide telecentric illumination of the sample 106. In this regard, the angular extent of illumination on the sample 106 may be limited to substantially parallel rays. By way of another example, an aperture stop located at a plane conjugate to a focal point of the objective lens 114 in the collection pathway 120 may provide telecentric imaging of the sample 106 such that the observed size of features may depend on distance from the objective lens 114 (e.g. the layer of the sample 106).

It is recognized herein that the precise position of a focal point of the objective lens 114 may vary based on wavelength (e.g. wavelength of the illumination spectrum or of radiation emanating from the sample 106) due to a number of factors including, but not limited to, chromatic aberrations. Accordingly, a layer-specific imaging configuration may include a precise location of an aperture stop in the illumination pathway 108 and/or the collection pathway 120 to adjust the telecentricity of illumination and/or imaging to be within a selected tolerance. For example, the imaging device 100 may include a positioning device 304 (e.g. coupled to the controller 126) to position an aperture as an aperture stop within the illumination pathway 108 and/or the collection pathway 120. The positioning device 304 may include any combination of elements suitable for positioning an aperture stop (e.g. aperture stop 302) in the imaging device 100, such as, but not limited to, a linearly translatable stage, a rotationally translatable stage, or the like.

Further, the imaging device 100 may include any number of optical elements for configuring illumination at a plane of an aperture stop. For example, as illustrated in FIG. 3, an illumination pathway 108 may include lenses 110*a* to focus an illumination beam 104 from an illumination source 102 at the plane of an aperture stop. Additionally, the illumination pathway 108 may include optical components 112 (e.g. polarizers, or the like) to further condition the illumination beam 104. By way of another example, an illumination pathway 108 may include lenses 110*b* to relay the plane of the aperture stop. For example, the lenses 110*b* may relay the back focal plane of the objective lens 114 such that the aperture stop 302 may be adjusted to provide telecentric illumination of the sample 106.

In another embodiment, the imaging device 100 includes one or more field stops. In a general sense, a field stop may limit the spatial extent of light in planes conjugate to the sample 106. For example, as illustrated in FIG. 3, a field stop 306 in the illumination pathway 108 may provide a layer-specific spatial extent of illumination on the sample 106. By way of another example, an aperture stop in the collection pathway 120 may provide a layer-specific limit of the spatial extent of radiation emanating from the sample 106 used to generate an image and thus provide a limit of the image size.

In another embodiment, a layer-specific imaging configuration includes an open diameter of a field stop in the illumination pathway 108 and/or the collection pathway 120. Accordingly, the imaging device 100 may include a field stop having an adjustable open diameter (e.g. coupled to the controller 126) for the generation of a layer-specific imaging configuration. It is recognized herein that adjusting the open diameter of a field stop may limit and/or define the portions of a sample that are imaged, which may facilitate high quality images by reducing unwanted and/or unnecessary light. For example, an open diameter of a field stop may be adjusted to illuminate and/or detect radiation from only a selected radius including features of interest on a given sample layer. In this regard, features outside this selected radius may not introduce noise to the image of features within the selected radius, which may facilitate images with high contrast, brightness, and the like.

It is further recognized herein that the precise position of planes conjugate to the sample 106 may vary based on wavelength (e.g. wavelength of the illumination spectrum or of radiation emanating from the sample 106) due to any number of factors such as, but not limited to, chromatic aberrations. Accordingly, a layer-specific imaging configuration may include a precise location of a field stop in the illumination pathway 108 and/or the collection pathway 120 to adjust the spatial extent of spatial extent of light in planes conjugate to the sample 106 within a selected tolerance. For example, the imaging device 100 may include a translation stage (e.g. coupled to the controller 126) to position an aperture as a field stop within the illumination pathway 108 and/or the collection pathway 120.

In another embodiment, a layer-specific imaging configuration includes a position of the sample stage 116 securing the sample 106. Accordingly, layer-specific imaging configuration may include a position of the sample 106 within a focal volume of the objective lens 114. In this regard, focusing conditions of the illumination beam 104 on the surface of or within the sample 106 may be tailored for each layer of interest.

In another embodiment, a layer-specific imaging configuration includes one or more imaging parameters of the detector 118. For example, the layer-specific imaging configuration may include, but is not required to include, selected settings of the gain, the integration time, or the like. Accordingly, images of different layers of interest may be captured using tailored detector settings to provide images having an image quality metric (e.g. brightness, contrast, noise level, position accuracy of features within the image, or the like) within a selected tolerance.

Figure 4:
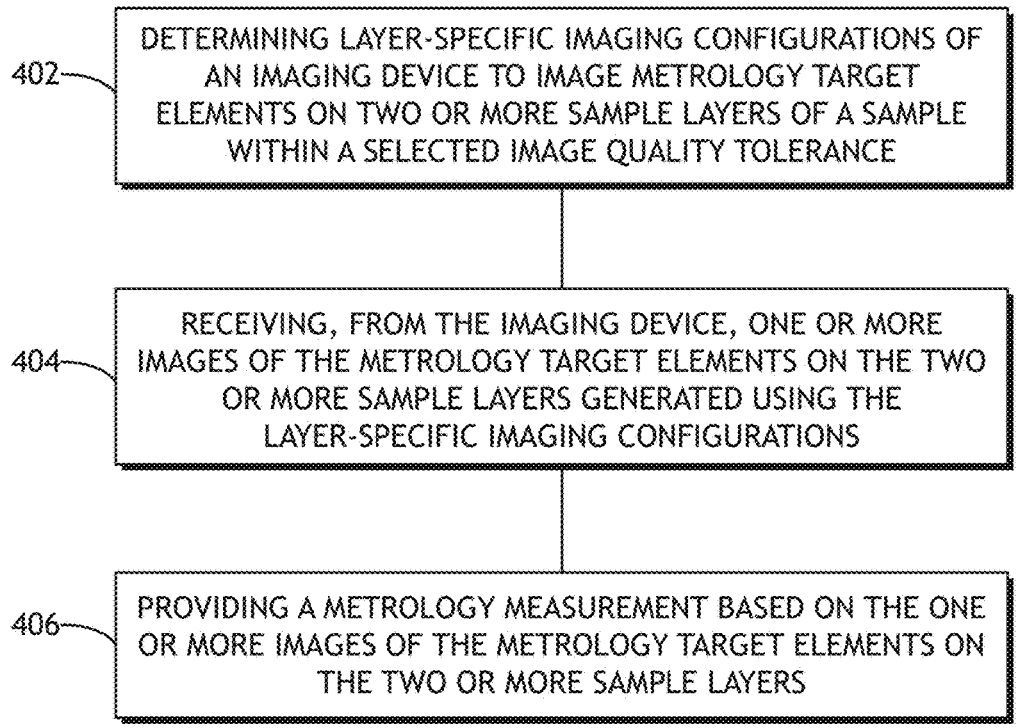
FIG. 4 is a flow diagram illustrating steps performed in a method for image-based metrology with layer-specific imaging configurations, in accordance with one or more embodiments of the present disclosure.

FIG. 4 is a flow diagram illustrating steps performed in a method 400 for image-based metrology with layer-specific imaging configurations, in accordance with one or more embodiments of the present disclosure. Applicant notes that the embodiments and enabling technologies described previously herein in the context of imaging device 100 should be interpreted to extend to method 400. It is further noted, however, that the method 400 is not limited to the architecture of imaging device 100.

In one embodiment, the method 400 includes a step 402 of determining (e.g. using controller 126, or the like) layer-specific imaging configurations of an imaging device to image metrology target elements on two or more sample layers of a sample within a selected image quality tolerance. The layer-specific imaging configuration may include, but is not limited to, any combination of an illumination spectrum incident on the sample, a detection spectrum of radiation incident, positions of aperture stops and/or field stops within the imaging device, Image quality metrics may include, but are not limited to, image brightness, image contrast, image noise, or the like. In this regard, an illumination spectrum may be tailored for each sample layer to provide images of features (e.g. metrology target elements) within a selected tolerance. In this regard, a selected tolerance may include a desired pixel intensity for one or more pixels in the image, a desired average pixel intensity, a desired difference between the maximum and minimum pixel intensities of an image, a desired amount of random variation of pixel intensity (e.g. noise), or the like.

For example, it may be the case that the imaging configuration may affect the image quality metrics such that the accuracy and/or repeatability of metrology measurements based on the generated images may vary. By way of another example, it may be the case that the imaging configuration may affect the sensitivity of metrology measurements (e.g. overlay measurements, feature size measurements, or the like) based on generated images to system imperfections due to misalignment, aberrations, or the like. Accordingly, providing a layer-specific imaging configuration may facilitate the generation of images having image quality within a selected tolerance and further facilitate metrology measurements that are accurate, repeatable and robust.

The layer-specific imaging configuration may include any combination of parameters of an imaging device. For example, the layer-specific imaging configuration may include a spectrum of illumination incident on the sample to generate an image. Features on each layer (e.g. metrology target elements) may thus be imaged with a tailored illumination spectrum suitable for providing an image having an image quality metric within a selected tolerance. Accordingly, the illumination spectrum may be, but is not required to be, adjusted for each layer of interest based on the properties of surrounding layers (e.g. the absorption, refractive index, thickness, or the like of surrounding layers).

By way of another example, the layer-specific imaging configuration may include a filtered spectrum of radiation emanating from the sample used to generate an image (e.g. a detection spectrum). In this regard, sample layers may be illuminated with a fixed illumination spectrum and layers of interest may be imaged with layer-specific detection spectra by filtering the radiation emanating from the sample prior to a detector.

By way of another example, the layer-specific imaging configuration may include an open diameter and/or a position of an aperture stop. In this regard, the layer-specific imaging configuration may include an angular extent of illumination incident on the sample and/or the angular extent of radiation emanating from the sample used to generate an image of a sample layer. In one instance, an aperture stop may be configured to provide telecentric illumination when positioned in a plane conjugate to the back focal plane of a collection lens (e.g. objective lens 114) in an illumination arm of the imaging system (e.g. the illumination pathway 108). In another instance, an aperture stop may be configured to provide telecentric imaging of the sample when positioned in a plane conjugate to the back focal plane of the collection lens in a collection arm of the imaging system (e.g. the collection pathway 120).

By way of another example, the layer-specific imaging configuration may include an open diameter and/or a position of a field stop. The layer-specific imaging configuration may thus include a spatial extent of illumination on the image and/or the spatial extent of radiation emanating from the sample directed to a detector to generate an image. In this regard, the layer-specific imaging configuration may include a specific portion of the sample to reduce unwanted and/or unnecessary light associated with portions of the sample not of interest for a given sample layer image.

By way of another example, the layer-specific imaging configuration may include a position of a sample within the focal volume of the imaging system (e.g. as controlled by a sample stage). For example, the focal position of the sample may be adjusted to compensate for differences in optical path between different sample layers, to compensate for chromatic aberration, or the like.

By way of another example, the layer-specific imaging configuration may include one or more detector settings associated with image generation. For example, the layer-specific imaging configuration may include, but is not required to include, selected values of gain, integration time, or the like of a detector tailored for each sample layer.

The layer-specific imaging configuration for each sample layer of interest determined in step 402 may be configured by any method known in the art suitable for providing images of sample layers of interest having image quality metrics within a specified tolerance. In one embodiment, the layer-specific imaging configurations are determined through a series of experiments in which potential imaging configuration parameters (e.g. illumination spectra, detection spectra, configurations of stops, focal positions of the sample, detector settings, or the like) are varied. In this regard, images of sample layers of interest (e.g. images of features of a metrology target on sample layers of interest) may be generated using a variety of candidate imaging configuration parameters. Image quality metrics for the sample layers of interest may be then compared for various combinations of imaging configuration parameters and the imaging configurations providing a desired set of image quality metrics may be selected for each sample layer of interest.

In another embodiment, the layer-specific imaging configurations may be selected by simulating images of sample layers of interest (e.g. images of features of a metrology target on sample layers of interest) and selecting the imaging configurations providing a desired set of image quality metrics for each sample layer of interest.

Further, step 402 may include simulating one or more metrology measurements based on images of sample layers (e.g. generated through measurements and/or by additional simulations) based on layer-specific image configurations.

Metrology measurements associated with metrology target elements on layers of the sample may include, but are not limited to, overlay measurements, critical dimension (CD) measurements, sidewall angles, film thicknesses. Further, one or more aspects of metrology target elements may be indicative of process-related parameters (e.g. focus, dose, and the like). The targets may include certain regions of interest that are periodic in nature, such as for example gratings in a memory die. The metrology targets may further possess various spatial characteristics and are typically constructed of one or more cells which may include features in one or more layers which may have been printed in one or more lithographically distinct exposures. The targets or the cells may possess various symmetries such as two-fold or four-fold rotation symmetry, reflection symmetry. Examples of such metrology structures are described in U.S. Pat. No. 6,985,618, which is included herein by reference in its entirety. Different cells or combinations of cells may belong to distinct layers or exposure steps. The individual cells may comprise either isolated non-periodic features or alternately they may be constructed from one, two or three dimensional periodic structures or combinations of non-periodic and periodic structures. The periodic structures may be non-segmented or they may be constructed from finely segmented features which may at or close to the minimum design rule of the lithographic process used to print them.

Simulations in step 402 may involve a number of algorithms. For example, optical interaction of the illumination beam 104 with a metrology target on the sample 106 may, but is not limited to, be modeled using an electro-magnetic (EM) solver. Further, the EM solver may utilize any method known in the art including, but not limited to, rigorous coupled-wave analysis (RCWA), finite element method analysis, method of moments analysis, a surface integral technique, a volume integral technique, or a finite-difference time-domain analysis. Additionally, collected data may be analyzed using data fitting and optimization techniques including, but not limited to libraries, fast-reduced-order models, regression, machine-learning algorithms such as neural networks, support-vector machines (SVM), dimensionality-reduction algorithms (e.g. principal component analysis (PCA), independent component analysis (ICA), local-linear embedding (LLE), and the like), sparse representation of data (e.g. Fourier or wavelet transforms, Kalman filters, algorithms to promote matching from same or different tool types, and the like). For example, data collection and/or fitting may be, but is not required to be, performed by the Signal Response Metrology (SRM) software product provided by KLA-TENCOR. In another embodiment, raw data generated by a metrology tool is analyzed by algorithms that do not include modeling, optimization and/or fitting (e.g. phase characterization, or the like).

It is noted herein that computational algorithms performed by the controller may be, but are not required to be, tailored for metrology applications through the use of parallelization, distributed computation, load-balancing, multi-service support, design and implementation of computational hardware, or dynamic load optimization. Further, various implementations of algorithms may be, but are not required to be, performed by the controller (e.g. though firmware, software, or field-programmable gate arrays (FPGAs), and the like), or one or more programmable optical elements associated with the metrology tool. The use of process modeling is generally described in U.S. Patent Publication No. 2014/0172394, published on Jun. 19, 2014, which is incorporated herein by reference in its entirety.

In another embodiment, the method 400 includes a step 404 of receiving, from the imaging device, one or more images of the metrology target elements on the two or more sample layers generated using the layer-specific imaging configurations. For example, the imaging system may generate images of sample layers of interest using the layer-specific imaging configurations.

In another embodiment, the method 400 includes a step 406 of providing a metrology measurement based on the one or more images of the metrology target elements on the two or more sample layers. The step 406 may include providing any type of metrology measurement known in the art based on the images of the two or more sample layers such as, but not limited to, overlay measurements associated with relative positions of features in different sample layers, or measurements of one or more aspects of features within each layer (e.g. size, orientation, or the like).

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A metrology system comprising:
an imaging device including:
a spectrally-tunable illumination device; and
a detector to generate images of a sample based on radiation emanating from the sample in response to illumination from the spectrally-tunable illumination device, the sample including metrology target elements on two or more sample layers; and
a controller communicatively coupled to the imaging device, the controller including one or more processors configured to execute program instructions configured to cause the one or more processors to:
determine layer-specific imaging configurations of the imaging device to image the metrology target elements on the two or more sample layers within a selected image quality tolerance, wherein each layer-specific imaging configuration includes an illumination spectrum from the spectrally-tunable illumination device;
receive, from the imaging device, one or more images of the metrology target elements on the two or more sample layers generated using the layer-specific imaging configurations; and provide a metrology measurement based on the one or more images of the metrology target elements on the two or more sample layers.

2. The metrology system of claim 1, wherein the layer-specific imaging configurations further include image acquisition parameters of the detector.

3. The metrology system of claim 2, wherein the image acquisition parameters of the detector include at least one of gain or integration time.

4. The metrology system of claim 1, wherein the imaging device includes an aperture stop having an adjustable position, wherein the layer-specific imaging configurations further include positions of the aperture stop to provide telecentric illumination of the sample within a selected telecentricity tolerance.

5. The metrology system of claim 1, wherein the imaging device includes an aperture stop having an adjustable position, wherein the layer-specific imaging configurations further include positions of the aperture stop to provide telecentric imaging of the sample within a selected telecentricity tolerance.

6. The metrology system of claim 1, wherein the imaging device includes a stage to position the sample at an adjustable focal position of the imaging device, wherein the layer-specific imaging configurations further include focal positions of the sample.

7. The metrology system of claim 1, wherein the spectrally-tunable illumination device sequentially provides two or more illumination spectra associated with the layer-specific imaging configurations of the imaging device, wherein the one or more images of the metrology target elements on the two or more sample layers includes separate images for the two or more sample layers, wherein the detector sequentially generates the separate images for the two or more sample layers based on the two or more illumination spectra.

8. The metrology system of claim 1, wherein the spectrally-tunable illumination device simultaneously provides two or more spatially-separated illumination spectra associated with the layer-specific imaging configurations of the imaging device to provide separate illumination spectra for the metrology target elements on the two or more sample layers, wherein the one or more images of the metrology target elements on the two or more sample layers generated by the detector includes a single image.

9. The metrology system of claim 1, wherein the spectrally-tunable illumination device comprises:
a broadband illumination source; and
one or more spectral filters to modify the spectrum of the broadband illumination source.

10. The metrology system of claim 9, wherein the one or more spectral filters comprise:
at least one of a short-pass filter, a long-pass filter, a bandpass filter, or a notch filter.

11. The metrology system of claim 9, wherein the one or more spectral filters comprise:
one or more spectral filters having fixed spectral filtering characteristics.

12. The metrology system of claim 11, wherein the spectrally-tunable illumination device further comprises:
at least one filter insertion device to selectively insert the one or more spectral filters having fixed spectral characteristics into a path of illumination from the broadband illumination source prior to the sample.

13. The metrology system of claim 12, wherein the filter insertion device comprises:

at least one of a filter wheel, a linear translation device, or a flipper device.

14. The metrology system of claim 9, wherein the one or more spectral filters comprise:
one or more spectral filters having tunable spectral filtering characteristics.

15. The metrology system of claim 14, wherein the one or more spectral filters having tunable spectral filtering characteristics comprise:
one or more angularly-tunable spectral filters having tunable spectral filtering characteristics based on an angle of incidence of illumination from the broadband illumination source, wherein the spectrally-tunable illumination device further comprises a filter tuning device to adjust the angle of incidence of illumination from the broadband illumination source on the one or more angularly-tunable spectral filters.

16. The metrology system of claim 14, wherein the one or more spectral filters having tunable spectral filtering characteristics comprise:
a tunable double monochromator.

17. The metrology system of claim 9, wherein the broadband illumination source comprises:
a supercontinuum laser source.

18. The metrology system of claim 9, wherein the broadband illumination source comprises:
at least one of a laser-pumped plasma illumination source or a lamp source.

19. The metrology system of claim 1, wherein the spectrally-tunable illumination device comprises:
two or more narrowband illumination sources; and
a selection device to select illumination from at least one of the two or more narrowband illumination sources for imaging the sample.

20. The metrology system of claim 19, wherein a narrowband illumination source of the two or more narrowband illumination sources comprises:
at least one of a laser source or a spectrally-filtered broadband illumination source.

21. The metrology system of claim 1, wherein the selected image quality tolerance comprises:
at least one of a contrast, resolution, brightness, or noise tolerance.

22. The metrology system of claim 1, wherein the detector comprises:
at least one of a charge coupled device detector or a complimentary metal-oxide-semiconductor detector.

23. The metrology system of claim 1, wherein the metrology measurement comprises:
an overlay measurement between the two or more sample layers.

24. The metrology system of claim 1, wherein the metrology measurement comprises:
critical dimensions of the metrology target elements on the two or more sample layers.

25. The metrology system of claim 1, wherein determining the layer-specific imaging configurations of the imaging device comprises:
generating, with the imaging device, images of the metrology target elements on each sample layer of the two or more sample layers using a variety of imaging conditions; and
selecting, for each sample layer of the two or more sample layers, a layer-specific imaging configuration from the variety of imaging configurations providing an image meeting the selected image quality tolerance.

26. The metrology system of claim 1, wherein determining the layer-specific imaging configurations of the imaging device comprises:
   simulating images of the metrology target elements on each sample layer of the two or more sample layers using a variety of imaging configurations; and
   selecting, for each sample layer of the two or more sample layers, a layer-specific imaging configuration from the variety of imaging configurations providing an image meeting the selected image quality tolerance.

27. A metrology system comprising:
   an imaging device including:
   a broadband illumination source;
   a spectrally-tunable filter to spectrally filter radiation emanating from a sample in response to illumination from the broadband illumination device; and
   a detector to generate images of the sample based on the radiation emanating from the sample and filtered by the spectrally-tunable filter, the sample including two or more sample layers; and
   a controller communicatively coupled to the imaging device, the controller including one or more processors configured to execute program instructions configured to cause the one or more processors to:
   determine layer-specific imaging configurations of the imaging device to image metrology target elements on the two or more sample layers within a selected image quality tolerance, wherein each layer-specific imaging configuration includes a spectrum of radiation from the sample filtered by the spectrally-tunable filter;
   receive, from the detector, one or more images of the metrology target elements on the two or more sample layers generated using the layer-specific imaging configurations; and
   provide a metrology measurement based on the one or more images of the metrology target elements on the two or more sample layers.

28. The metrology system of claim 27, wherein the layer-specific imaging configurations further include image acquisition parameters of the detector.

29. The metrology system of claim 28, wherein the image acquisition parameters of the detector include at least one of gain or integration time.

30. The metrology system of claim 27, wherein the imaging device includes an aperture stop having an adjustable position, wherein the layer-specific imaging configurations further include positions of the aperture stop to provide telecentric illumination of the sample within a selected telecentricity tolerance.

31. The metrology system of claim 27, wherein the imaging device includes an aperture stop having an adjustable position, wherein the layer-specific imaging configurations further include positions of the aperture stop to provide telecentric imaging of the sample within a selected telecentricity tolerance.

32. The metrology system of claim 27, wherein the imaging device includes a stage to position the sample at an adjustable focal position of the imaging device, wherein the layer-specific imaging configurations further include focal positions of the sample.

33. The metrology system of claim 27, wherein the spectrally-tunable filter sequentially provides two or more filtered spectra associated with the layer-specific imaging configurations of the imaging device, wherein the one or more images of the metrology target elements on the two or more sample layers includes separate images for the two or more sample layers, wherein the detector sequentially generates the separate images for the two or more sample layers based on the two or more filtered spectra.

34. The metrology system of claim 27, wherein the spectrally-tunable filter simultaneously provides two or more spatially-separated illumination spectra associated with the layer-specific imaging configurations of the imaging device to provide separate illumination spectra for the metrology target elements on the two or more sample layers, wherein the one or more images of the metrology target elements on the two or more sample layers generated by the detector includes a single image.

35. The metrology system of claim 27, wherein the spectrally-tunable filter comprises:
   at least one of a short-pass filter, a long-pass filter, a bandpass filter, or a notch filter.

36. The metrology system of claim 27, wherein the spectrally-tunable filter comprises:
   one or more spectral filters having fixed spectral filtering characteristics.

37. The metrology system of claim 36, wherein the spectrally-tunable filter further comprises:
   at least one filter insertion device to selectively insert the one or more spectral filters having fixed spectral characteristics into a path of radiation emanating from the sample prior to the detector.

38. The metrology system of claim 37, wherein the filter insertion device comprises:
   at least one of a filter wheel, a linear translation device, or a flipper device.

39. The metrology system of claim 27, wherein the spectrally-tunable filter comprises:
   one or more spectral filters having tunable spectral filtering characteristics.

40. The metrology system of claim 39, wherein the one or more spectral filters having tunable spectral filtering characteristics comprise:
   one or more angularly-tunable spectral filters having tunable spectral filtering characteristics based on an angle of incidence of illumination from the broadband illumination source, wherein the imaging device further comprises a filter tuning device to adjust the angle of incidence of illumination from the broadband illumination source on the one or more angularly-tunable spectral filters.

41. The metrology system of claim 27, wherein the broadband illumination source comprises:
   a supercontinuum laser source.

42. The metrology system of claim 27, wherein the broadband illumination source comprises:
   at least one of a laser-pumped plasma illumination source or a lamp source.

43. The metrology system of claim 27, wherein the selected image quality tolerance comprises:
   at least one of a contrast, resolution, brightness, or noise tolerance.

44. The metrology system of claim 27, wherein the detector comprises:
   at least one of a charge coupled device detector or a complimentary metal-oxide-semiconductor detector.

45. The metrology system of claim 27, wherein the metrology measurement comprises:
   an overlay measurement between the two or more sample layers.

46. The metrology system of claim 27, wherein the metrology measurement comprises:
   critical dimensions of the metrology target elements on the two or more sample layers.

47. The metrology system of claim 27, wherein determining the layer-specific imaging configurations of the imaging device comprises:
generating, with the imaging device, images of the metrology target elements on each sample layer of the two or more sample layers using a variety of imaging conditions; and
selecting, for each sample layer of the two or more sample layers, a layer-specific imaging configuration from the variety of imaging configurations providing an image meeting the selected image quality tolerance.

48. The metrology system of claim 27, wherein determining the layer-specific imaging configurations of the imaging device comprises:
simulating images of the metrology target elements on each sample layer of the two or more sample layers using a variety of imaging configurations; and
selecting, for each sample layer of the two or more sample layers, a layer-specific imaging configuration from the variety of imaging configurations providing an image meeting the selected image quality tolerance.

49. A method comprising:
determining, with one or more processors, layer-specific imaging configurations of an imaging device to image metrology target elements on two or more sample layers of a sample within a selected image quality tolerance, wherein each layer-specific imaging configuration includes an imaging spectrum;
receiving, from the imaging device, one or more images of the metrology target elements on the two or more sample layers generated using the layer-specific imaging configurations; and
providing a metrology measurement based on the one or more images of the metrology target elements on the two or more sample layers.

50. The method of claim 49, wherein the imaging spectrum of the layer-specific imaging configurations includes a spectrum of illumination incident on the sample.

51. The method of claim 49, wherein the imaging spectrum of the layer-specific imaging configurations includes a spectrum of radiation incident on a detector of the imaging device to generate the one or more images of the metrology target elements on the two or more sample layers.

52. The method of claim 51, wherein the layer-specific imaging configurations further include image acquisition parameters of the detector.

53. The method of claim 52, wherein the image acquisition parameters of the detector include at least one of gain or integration time.

54. The method of claim 49, wherein the imaging device includes an aperture stop having an adjustable position, wherein the layer-specific imaging configurations further include positions of the aperture stop to provide telecentric illumination of the sample within a selected telecentricity tolerance.

55. The method of claim 49, wherein the imaging device includes a stage to position the sample at an adjustable focal position of the imaging device, wherein the layer-specific imaging configurations further include focal positions of the sample.

56. The method of claim 49, wherein determining the layer-specific imaging configurations of the imaging device comprises:
generating, with the imaging device, images of the metrology target elements on each sample layer of the two or more sample layers using a variety of imaging conditions; and
selecting, for each sample layer of the two or more sample layers, a layer-specific imaging configuration from the variety of imaging configurations providing an image meeting the selected image quality tolerance.

57. The method of claim 49, wherein determining the layer-specific imaging configurations of the imaging device comprises:
simulating images of the metrology target elements on each sample layer of the two or more sample layers using a variety of imaging configurations; and
selecting, for each sample layer of the two or more sample layers, a layer-specific imaging configuration from the variety of imaging configurations providing an image meeting the selected image quality tolerance.

* * * * *